United States Patent [19]

Andersson et al.

[11] Patent Number: 4,804,656

[45] Date of Patent: Feb. 14, 1989

[54] NOVEL ANDROSTANE-17β-CARBOXYLIC ACID ESTERS

[75] Inventors: Paul H. Andersson, Sodra Sandby; Per T. Andersson, Lund; Bengt I. Axelsson, Genarp; Bror A. Thalen, Bjärred; Jan W. Trofast, Lund, all of Sweden

[73] Assignee: Aktiebolaget Draco, Lunc, Sweden

[21] Appl. No.: 847,933

[22] Filed: Apr. 3, 1986

Related U.S. Application Data

[63] Continuation-in-part of Ser. No. 843,768, Mar. 25, 1986, abandoned.

[30] Foreign Application Priority Data

Apr. 4, 1985 [SE] Sweden ............................ 8501692
Jun. 13, 1985 [SE] Sweden ............................ 8502932

[51] Int. Cl.$^4$ .......................... A61K 31/56; C07J 1/00
[52] U.S. Cl. .................................. 514/179; 514/180; 260/397.45
[58] Field of Search .................... 514/179, 180; 200/397.45

[56] References Cited

U.S. PATENT DOCUMENTS

| | | | |
|---|---|---|---|
| 3,828,080 | 8/1974 | Phillipps et al. | 260/397.1 |
| 3,981,894 | 9/1976 | Phillipps et al. | 260/397.1 |
| 4,710,495 | 12/1987 | Bodor | 260/397.45 |

OTHER PUBLICATIONS

Chemical Abstracts; vol. 96 (1982), #163044p; Glaxo Group Ltd.
Chemical Abstracts; vol. 80 (1974), #121208j; Phillips et al.
Chemical Abstracts; vol. 101 (1984), #1027e, Manz et al.
Chemical Abstracts; vol. 97 (1982), #6651n, Bodor.

*Primary Examiner*—Leonard Schenkman
*Assistant Examiner*—Joseph A. Lipoysky
*Attorney, Agent, or Firm*—Brumbaugh, Graves, Donohue & Raymond

[57] ABSTRACT

The invention refers to compounds having anti-inflammatory activity characterized by the formula

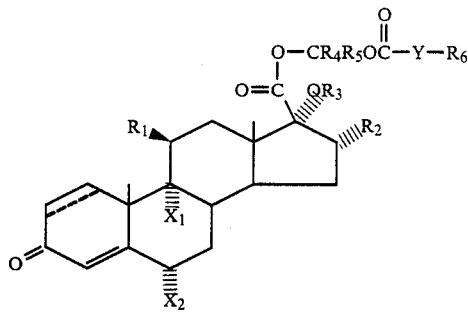

or a stereoisomeric component thereof, in which formula $X_1$ represents a hydrogen, chlorine, bromine or fluorine atom;

$X_2$ represents a hydrogen, chlorine, bromine or fluorine atom;

$R_1$ represents a β-hydroxy group, a β-chlorine atom or an oxo group;

$R_2$ represents a hydrogen atom, a methylene group or an α- or β-methyl group;

$R_3$ represents a hydrogen atom or an acyl group of 1 through 8 carbon atoms;

$R_4$ represents a hydrogen atom, a ($C_1$–$C_5$) alkyl group or a phenyl group;

$R_5$ represents a hydrogen atom, a ($C_1$–$C_5$) alkyl group or a phenyl group;

Y represents either $CR_7R_8$, O, S or $NR_9$, where $R_7$, $R_8$ and $R_9$ are selected from hydrogen or from straight or branched hydrocarbon chains having 1–8 carbon atoms or from a phenyl group.

$R_6$ represents a hydrogen; a methyl group; a phenyl or an alkenyl or cycloalkylene group optionally substituted by alkyl, nitro, carboxy, alkoxy, halogen, cyano, carbalkoxy and trifluoromethyl group(s); a ($C_1$–$C_5$) alkyl group substituted by at least one halogen atom; a saturated or unsaturated carbocyclic or heterocyclic (O, S, N) ring system containing 3–10 atoms in the ring system; a $C_1$ alkyl group substituted by either one or two alicyclic or aromatic 3,4,5 or 6-numbered ring system(s) or one, two or three straight or branched alkyl or alkenyl group(s) of 1 through 18 carbon atoms; and represents a single or double bond.

The invention also refers to a process and intermediates for the preparation of these compounds, a pharmaceutical preparation containing one of the compounds and a method for the treatment of inflammatory conditions.

8 Claims, No Drawings

NOVEL ANDROSTANE-17β-CARBOXYLIC ACID ESTERS

This application is a continuation-in-part of application Ser. No. 843,768 filed Mar. 25, 1986 now abandoned.

DESCRIPTION

1. Field of the Invention

The present invention relates to novel anti-inflammatory and antiallergic glucocorticosteroids and to intermediates and processes for their preparation. The invention also relates to pharmaceutical compositions containing the compounds and to methods of treatment of inflammatory, allergic, muscoskeletal or dermatological conditions with these compounds.

The object of the invention is to provide an anti-inflammatory and anti-allergic androstane-17β-carboxylic acid ester for the administration to the site of inflammation. The steroid ester will be rapidly metabolised and as a consequence systemic effects will be reduced.

2. Background Art

THe glucocorticosteroids are one of the most potent and widely used classes of anti-inflammatory substances known. They are extremely effective in preventing or reducing the severity of a wide spectrum of inflammatory, immunologic and allergic diseases in the respiratory tract (e.g. asthma, rhinitis), in the skin (e.g. eczema, psoriasis) or in the bowel (e.g. ulcerative colitis, Morbus Crohn). There is, however, a general desire to minimize the systemic side effects. One way of doing this involves application of the steroid locally to the organ to be treated, e.g. the respiratory tract, so allowing smaller systemic concentrations of the steriod. A rapid inactivation by e.g. hydrolysis in the target organ or in the general circulation will further decrease the systemic side effects.

DISCLOSURE OF THE INVENTION

The steroid compounds with which the invention is concerned are compounds of the general formula:

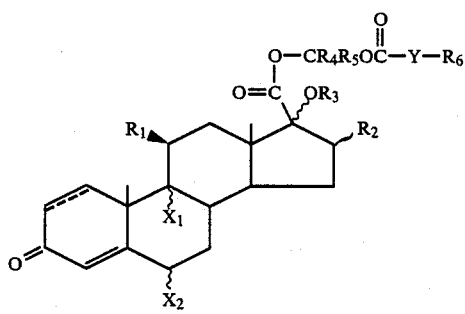

wherein $X_1$ represents a hydrogen, chlorine, bromine or fluorine atom;

$X_2$ represents a hydrogen, chlorine, bromine or fluorine atom;

$R_1$ represents a β-hydroxy group, a β-chlorine atom or an oxo group;

$R_2$ represents a hydrogen atom, a methylene group or an α- or β-methyl group;

$R_3$ represents a hydrogen atom or an acyl group of 1 through 8 carbon atoms;

$R_4$ represents a hydrogen atom, a ($C_1$–$C_5$) alkyl group or a phenyl group;

$R_5$ represents a hydrogen atom, a ($C_1$–$C_5$) alkyl group or a phenyl group;

Y represents either $CR_7R_8$, O, S, or $NR_9$, where $R_7$, $R_8$ and $R_9$ are selected from hydrogen or from straight or branched hydrocarbon chains having 1–8 carbon atoms of from a phenyl group;

$R_6$ represents a hydrogen; a methyl group; a phenyl or an alkenyl or cycloalkenyl group optionally substituted by alkyl, nitro, carboxy, alkoxy, halogen, cyano, carbalkoxy and trifluoromethyl group(s); a ($C_1$–$C_5$) alkyl group substituted by at least one halogen atom; a saturated or unsaturated carbocyclic or heterocyclic (O, S, N) ring system containing 3–10 atoms in the ring system; a $C_1$ alkyl group substituted by either one or two alicyclic or aromatic 3, 4, 5 or 6-numbered ring system(s) or one, two or three straight or branched alkyl or alkenyl group(s) of 1 through 18 carbon atoms; and ═══represents a single or double bond.

In general, the group $R_6$ in formula I is preferably an alkyl group containing 1 to 5 carbon atoms, advantageously a methyl, ethyl, propyl, allyl, isopropyl, methallyl, isobutyl, cyclopropylmethyl, cyclobutyl, or cyclopentyl group.

The halogen atom for position $X_1$ and $X_2$ is preferably a fluorine or chlorine atom; the acyl group ($R_3$) is preferably an acetyl, propionyl, butyryl or valeroyl group. $R_1$ generally represents a β-hydroxy group and ═══ generally represents a double bond.

Of the subgroup

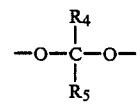

the compounds wherein $R_4$=H and $R_5$=methyl or $R_4$=methyl and $R_5$=H are preferred.

A preferred class of compounds of formula I having particularly good pharmacological activity include the following esters of 9α-fluoro-11β-hydroxy-16β-methyl-3-oxo-17α-propionyloxy-androsta-1,4-diene-17β-carboxylic acid and 9α-chloro-11β-hydroxy-16β-methyl-3-oxo-17α-propionyloxy-androsta-1,4-diene-17β-carboxylic acid:

1'-ethoxycarbonyloxyethyl, 1'-isopropoxycarbonyloxyethyl, 1'-propoxycarbonyloxyethyl, 1'-cyclopropylmethoxycarbonyloxyethyl, 1'-cyclobutoxycarbonyloxyethyl, 1'-isobutoxycarbonyloxyethyl, 1'-cyclopentoxycarbonyloxyethyl, 1'-(2-chlorethoxy)-carbonyloxyethyl and 1'-acetoxyethyl.

Methods of preparation

Epimers resulting from the asymmetric centre in the ester group of formula I constitute a further aspect of the invention and the invention includes the preparation of such epimers as well as mixtures thereof. The epimers possess practically identical solubility characteristics. Accordingly, they have been impossible to separate and isolate from the epimeric mixture by conventional methods for resolution of stereoisomers, e.g. fractionated crystallisation. However, the epimers can be separated in view of different mobility on the stationary phase in a chromatographic system. The separation may be carried out for instance on Silica or particularly on cross-linked dextran gels of the type Sephadex ® LH, e.g. Sephadex ® LH-20 with a suitable organic solvent as eluting agent. As eluting agent on a Sephadex ® LH-20 column, a halogenated hydrocarbon such as chloroform or a mixture of heptane-chloroform-ethanol in the proportions 0–50:50–100:10–1 has successfully been used, preferably a 20:20:1 mixture. In these straight phase chromatography systems the epimers have arbitrarily been designed A and B respectively, in order of elution from the column.

Starting material

The 17β-carboxylic acid starting materials are prepared by eliminating the 21 carbon atom from a suitable 21-hydroxy-3,20-dioxopregn-4-ene or pregna-1,4-diene. This is readily accomplished by any means known in the art such as using sodium hypobromate, sodium bismuthate, sodium periodate or oxygen (air) in alkaline solution. Preferably, the oxidation is carried out with periodic acid, in a solvent medium such as tetrahydrofuran/$H_2O$ and preferably at room temperature. Suitable 21-hydroxy-3,20-dioxopregn-4-enes or pregna-1,4-dienes include known compounds such as betamethasone, dexamethasone, paramethasone, beclomethasone, flumethasone and the like. By following procedures generally known in the art steroids of a relatively simple structure can be converted to other structures as desired.

The esterification of the 17α-hydroxy group in the preparation of the new androstane compounds may be effected in known manner, e.g. by reacting the parent 17α-hydroxy compound with an appropriate carboxylic acid or a reactive derivative thereof, such as an acid anhydride, acid halide or orthoester in the presence of a suitable acid catalyst and a solvent at temperatures of 20° to 100° C. Suitable carboxylic acids and reactive derivatives include e.g. acetic acid, propionic acid, butyric acid etc. and the corresponding acid anhydrides and acid halides and orthoesters. Solvents include non-hydroxylic solvents such as methylene chloride, chloroform, benzene and the like, while suitable acid catalysts include p-toluene-sulfonic acid, sulfosalicyclic acid, perchloric acid, strongly acidic cation exchange resins and the like.

For the preparation of the 17α-esters of the 17β-carboxylic acids which may be employed in the preparation of the compounds according to the invention, it is often preferred to treat the parent 17α-hydroxy-17β-carboxylic acid with appropriate acid anhydride or acid halide to give the mixed anhydride of the androstane 17β-carboxylic acid and the carboxylic ester of the starting acid anhydride or acid halide, this reaction being conveniently effected at an elevated temperature, the resulting anhydride then being solvolysed under acidic conditions (e.g. using aqueous acetic acid) or under basic conditions (e.g. aqueous pyridine or a secondary amine such as diethylamine in acetone).

End compounds

The compounds of the invention may be obtained by any of the following methods.

The esters may be prepared by reacting the 17β-carboxylic acid in the form of a salt, for instance an alkali metal salt or a tetraethyl ammonium or tetrabutyl ammonium salt with a halogen ester having the formula:

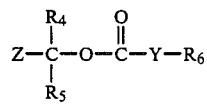

wherein Y, $R_6$, $R_4$, $R_5$ have the same meaning as above and Z is a halogen atom, preferably a chlorine or bromine atom, or a functionally equivalent group such as a sulphonyloxy radical. The reaction is carried out in an inert organic solvent, for instance acetone, methylethylketone, dimethylformamide, dimethylsulphoxide, methylene chloride or chloroform, and at temperatures between 0° and 100° C. The reaction may also be performed in the presence of a crown ether.

Pharmaceutical preparations

The compounds of the invention may be used for different modes of local administration dependent on the site of inflammation, e.g. percutaneously, parenterally or for local administration in the respiratory tract by inhalation. An important aim of the formulation design is to reach optimal bioavailability of the active steroid ingredient. For percutaneous formulations this is advantageously achieved if the steroid is dissolved with a high thermodynamic activity in the vehicle. This is attained by using a suitable system of solvents comprising suitable glycols, such as propylene glycol or 1,3-butandiol either as such or in combination with water.

It is also possible to dissolve the steroid either completely or partially in a lipophilic phase with the aid of a surfactant as a solubilizer. The percutaneous compositions can be an ointment, an oil in water cream, a water in oil cream or a lotion. In the emulsion vehicles the system comprising the dissolved active component can make up the disperse phase as well as the continuos one. The steroid can also exist in the above compositions as a micronized, solid substance.

Pressurized aerosols for steroids are intended for oral or nasal inhalation. The aerosol system is designed in such a way that each delivered dose contains 10–1000 μg, preferbly 20–250 μg of the active steriod. The most active steroids are administered in the lower part of the dose range. The micronized steroid consists of particles substantially smaller than 5 μm, which are suspended in a propellent mixture with the assistance of a dispersant, such as sorbitan trioleate, oleic acid, lecithin or sodium salt of dioctylsulphosuccinic acid.

WORKING EXAMPLES

The invention is further illustrated by the following examples to which it is not limited. All the mass spectra have been obtained by chemical ionization mass spectrometry and they are all in agreement with the molecular weights of the compounds. The purity of each epimer has been determined on a HPLC (High Performance Liquid Chromatography) system using a μBondapak $C_{18}$ column (300×3.9 mm i.d.) with a flow rate of 1.0 ml/min and with ethanol-water in ratio between 35:65 and 65:35 as the mobile phase.

EXAMPLES

The compounds given in table 1 were prepared, isolated and purified in a manner analogous to the procedure described in examples 1–5.

EXAMPLE 1

Preparation of 1'-ethoxycarbonyloxyethyl 9α-fluoro-11β-hydroxy-16β-methyl-3-oxo-17α-propionyloxyandrosta-1,4-diene-17β-carboxylate A mixture of betamethasone (4.0 g) in tetrahydrofurane (45 ml) and periodic acid (7.0 g) dissolved in water (25 ml) is stirred at room temperature for 2 hrs. Water (40 ml) is added and the organic solvent is eliminated under reduced pressure. The resulting crystalline precipitate is collected by filtration, washed with water and dried to give 9α-fluoro-11β,17α-dihydroxy-16β-methyl-3-oxo-androsta-1,4-diene-17β-carboxylic acid (4.0 g).

The acid is suspended in methylene chloride (80 ml) and triethylamine (4.1 ml) and propionyl chloride (3.5 ml) are added at 0° C. After being stirred at 0° C. for 80 min the reaction mixture is diluted with methylene chloride and washed successively with 3% sodium bicarbonate, 2N hydrochloric acid and water, and then dried and evaporated in vacuo.

The solid is treated with diethylamine (3.0 ml) in acetone (130 ml) for 90 min at room temperature. After evaporation of the organic solvent, water is added and the mixture is extracted with ethyl acetate. Acidification with 2N hydrochloride acid and extraction with ethyl acetate gives after the usual work-up 9α-fluoro-11β-hydroxy-16β-methyl-3-oxo-17α-propionyloxyandrosta-1,4-diene-17β-carboxylic acid as a white crystalline solid (3.8 g).

Modification 1

A mixture of 9α-fluoro-11β,17α-dihydroxy-16β-methyl-3-oxo-androsta-1,4-diene-17β-carboxylic acid (2.5 g), potassium bicarbonate (800 mg), 18-crown-6 (10.5 mg) and α-chloroethyl ethyl carbonate (1.2 g) in dimethyl formamide (50 ml) is stirred at 80° C. for 3 hrs. The reaction mixture is diluted with 10% sodium chloride (200 ml) and extracted with methylene chloride (3×100 ml). The organic phase is washed successively with 5% sodium bicarbonate (100 ml) and water (3×75 ml), dried and evaporated in vacuo.

Chromatography on Sephadex® LH-20 with chloroform gives the epimeric mixture of the title compound.

A further chromatographic step on Sephadex® LH-20 with heptane-chloroform-ethanol (20:20:1) gives the pure epimers with good purity as examined by HPLC-analysis.

Epimer A: 1.14 g (72%) M.p. 187°–90° C. $[\alpha]_D^{25} = +86.7°$ (c=0.2, $CH_2Cl_2$)

HPLC-analysis of epimer A: 99.3% p MS-CI ($CH_4$): $MH^+ = 551$; $M^+ + 29 = 579$ NMR ($^1H$): 6.71 ppm, quartet

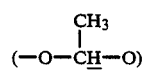

Epimer B: 1.27 g (80%) M.p. 218°–21° C. $[\alpha]_D^{25} = +0.9°$ (c=0.2, $CH_2Cl_2$)

HPLC-analysis of epimer B: 99.2%
MS-CI ($CH_4$): $MH^+ = 551$; $M^+ + 29 = 579$
NMR ($^1H$): 6.81 ppm, quartet

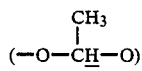

Modification 2

By running the esterification step at 80° C. for 3 hrs but without the presence of 18-crown-6 a yield of 84% of the epimeric mixture of the title compound was obtained. Otherwise identical conditions as in method 1.

Modification 3

A mixture of 9α-fluoro-11β-hydroxy-16β-methyl-3-oxo-17α-propionyloxyandrosta-1,4-diene-17β-carboxylic acid (435 mg), potassium bicarbonate (111 mg) and α-bromoethyl ethyl carbonate (209 mg) in acetonitrile (50 ml) is stirred at 40° C. for 5 hours. The solvent is evaporated in vacuo and the residue is dissolved in methylene chloride. The organic phase is washed successively with 5% sodium bicarbonate and water, dried and evaporated in vacuo. Chromatographic work-up as in method A gives the pure epimers A (155 mg) and B (170 mg) of 1'-ethoxycarbonyloxyethyl 9α-fluoro-11β-hydroxy-16β-methyl-3-oxo-17α-propionyloxyandrosta-1,4-diene-17β-carboxylate.

The reaction may as well be performed in any aprotic solvent such as dimethylformamide or dimethylsulfoxide.

Modification 4

A mixture of 9α-fluoro-11β-hydroxy-16β-methyl-3-oxo-17α-propionyloxyandrosta-1,4-diene-17β-carboxylic acid (250 mg), potassium bicarbonate (69 mg), α-chloroethyl ethyl carbonate (102 mg) and lithium bromide (240 mg) in acetone (25 ml) was refluxed for 17 hours. Using the work-up procedure in method A gave the epimeric mixture of 1'-ethoxycarbonyloxyethyl 9α-fluoro-11β-hydroxy-16β-methyl-3-oxo-17α-propionyloxyandrosta-1,4-diene-17β-carboxylate (20 mg). When a mixture of a α-chloroethyl ethyl carbonate (1.5 g) and lithium bromide (3.4 g) was refluxed in acetone (20 ml) for 2 hours, an oil (0.8 g) of α-chloroethyl ethyl carbonate (58%) and α-bromoethyl ethyl carbonate (42%) was obtained.

Modification 5

To the potassium salt of 9α-fluoro-11β-hydroxy-16β-methyl-3-oxo-17α-propionyloxyandrosta-1,4-diene-17β-carboxylic acid (475 mg) in methylene chloride (20 ml) and water (10 ml) was added tetrabutylammonium hydrogensulfate (340 mg) with stirring. pH was adjusted to 7 with 2M sodium hydroxide. The organic phase was evaporated. The residue was dissolved in acetone (50 ml) and α-chloroethyl ethyl carbonate (150 mg) was added. The solution was stirred for 4 hours at 50° C. The acetone was removed by vakuum and the residue was extracted with n-butyl acetate, the organic phase washed with 3% sodium bicarbonate and twice with water, dried and evaporated. Using the same chromatographic procedure as in Method 1 gave the pure epimers (A: 81 mg; B: 83 mg) of the title compound.

Modification 6

To a solution of 9α-fluoro-11β-hydroxy-16β-methyl-3-oxo-17α-propionyloxyandrosta-1,4-diene-17β-carboxylic acid (451 mg), 1,5-diazabicyclo[5.4.0]undecene-5 (152 mg) in bensene (10 ml) was added α-chloroethyl ethyl carbonate (152 mg) in bensene (5 ml). The solution was stirred under reflux for 6 hours, and thereafter over night at room tempertaure. The solvent was removed by vakuum and the residue dissolved in methylene chloride, washed with sodium bicarbonate in twice with water, dried and evaporated. Using the same chromatographic procedure as in Method 1 gave the pure epimers (A: 48 mg, B: 55 mg) of the title compound.

EXAMPLE 2

Preparation of 1'-isopropylcarbamoyloxyethyl 9α-fluoro-11β-hydroxy-16β-methyl-3-oxo-17α-propionyloxyandrosta-1,4-diene-17β-carboxylate Treatment of 9α-fluoro-11β-hydroxy-16β-methyl-3-oxo-17α-propionyloxyandrosta-1,4-diene-17β-carboxylic acid (1.4 g) with potassium bicarbonate (450 mg) and 1'-chloroethyl isopropylcarbamate (695 mg; prepared from α-chloroethyl chloroformate and isopropylamine in diethylether) in dimethylformamide (30 ml) at 80° C. for 3 hrs following the same work up procedure as in Example 1 afforded epimer A (110 mg; m.p. 210°-14°; HPLC: 99.7%, NMR ($^1$H): 6.69 ppm (quartet, O—CH(CH$_3$)—O—); MS-CI (CH$_4$): MH$^+$: 564, M$^+$+29=592) and epimer B (28 mg; m.p. 183°-86°; HPLC: 99.1%; NMR ($^1$H): 6.81 ppm (quartet, —O—CH(CH$_3$)—O—); MS-CI (CH$_4$): MH$^+$: 564, M$^+$+29=592) of 1'-isopropylcarbamoyloxyethyl 9α-fluoro-11β-hydroxy-16β-methyl-3-oxo-17α-propionyloxyandrosta-1,4-diene-17β-carboxylate.

EXAMPLE 3

Preparation of 1'-diethylcarbamoyloxymethyl 9α-fluoro-11β-hydroxy-16β-methyl-3-oxo-17α-valeroyloxyandrosta-1,4-diene-17β-carboxylate Reaction of 9α-fluoro-11β-hydroxy-16β-methyl-3-oxo-17α-valeroyloxyandrosta-1,4-diene-17β-carboxylic acid (1.1 g) with potassium bicarbonate (10 g) and 1'-chloroethyl diethylcarbamate (825 mg; prepared from α-chloroethyl chloroformate and diethylamine in diethylether) in dimethylformamide (20 ml) at room temperature for 48 hrs following the same work up procedure as in example 1 afforded epimer A (120 mg; m.p. 184°-87°; HPLC: 99.8%; NMR ($^1$H): 6.71 ppm (quartet, —O—CH(CH$_3$)—O—); MS-CI (CH$_4$): MH$^+$: 606, M$^+$+29=634) and epimer B (104 mg, m.p. 156°-60°; HPLC: 99.8%; NMR ($^1$H): 6.81 ppm (quartet, —O—CH(CH$_3$)—O—); MS-CI (CH$_4$): MH$^+$: 606, M$^+$+29=634) of 1'-diethylcarbamoyloxyethyl 9α-fluoro-11β-hydroxy-16β-methyl-3-oxo-17α-valeroyloxyandrosta-1,4-diene-17β-carboxylate.

EXAMPLE 4

Preparation of 1'-acetyloxyethyl 9α-fluoro-11β-hydroxy-16β-methyl-3-oxo-17α-propionyloxyandrosta-1,4-diene-17β-carboxylate Treatment of 9α-fluoro-11β-hydroxy-16β-methyl-3-oxo-17α-propionyloxyandrosta-1,4-diene-17β-carboxylic acid (1.2 g) with potassium bicarbonate (1.2 g) and α-chloroethyl acetate (1.2 g; prepared from acetylchloride, paraldehyde and zinkchloride under nitrogen at −10° C. for 2 hrs) in dimethylformamide (40 ml) at 50° C. for 20 hrs following the same work up procedure as in Example 1 afforded epimer A (391 mg; HPLC: 99.7%; NMR ($^1$H): 6.79 ppm (quartet, —O—CH(CH$_3$)—O—); MS-CI (CH$_4$): MH$^+$: 521, M$^+$+29=549) and epimer B (393 mg; mp 211°-2°; HPLC: 99.8%; NMR ($^1$H): 6.93 ppm (quartet, —O—CH(CH$_3$)—O—); MS-CI (CH$_4$): MH$^+$: 521, M$^+$+29=549) of 1'-acetyloxyethyl 9α-fluoro-11β-hydroxy-16β-methyl-3-oxo-17α-propionyloxyandrosta-1,4-diene-17β-carboxylate.

EXAMPLE 5

Preparation of 1'-isopropylthiocarbonyloxyethyl 9α-fluoro-11β-hydroxy-16β-methyl-3-oxo-17α-propionyloxyandrosta-1,4-diene-17β-carboxylate Treatment of 9α-fluoro-11β-hydroxy-16β-methyl-3-oxo-17α-propionyloxyandrosta-1,4-diene-17β-carboxylic acid (1.0 g) with potassium bicarbonate (350 mg) and α-chloroethyl-5-isopropyl thiocarbonate (600 mg; prepared from α-chloroethyl chloroformate and 2-propanethiol (in pyridine and diethylether) in dimethylformamide (20 ml) at room temperature for 48 hours following the same work up procedure as in example 1 afforded epimer A (14 mg; NMR ($^1$H): 6.92 ppm (quartet, —O—CH(CH$_3$)—O—); MS-CI (CH$_4$); M$^+$=581; M$^+$+29=609) and epimer B (18 mg); NMR ($^1$H): 6.98 ppm (quartet, —O—CH(CH$_3$)—O—); MS-CI (CH$_4$): MH$^+$=581) 1'-isopropylthiocarbonyloxyethyl 9α-fluoro-11β-hydroxy-16β-methyl-3-oxo-17α-propionylandrosta-1,4-diene-17β-carboxylate.

TABLE 1

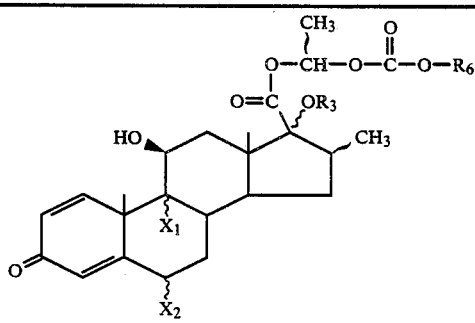

| Ex. No. | X$_1$ | X$_2$ | 16-Me | R$_3$ | R$_6$ | Epimer | M.p. °C. | $[\alpha]_D^{25}$ (c = 0.2 in CH$_2$Cl$_2$) | Empirical formula | Mol. weight | HPLC % purity |
|---|---|---|---|---|---|---|---|---|---|---|---|
| 6a | F | H | β | COCH$_2$CH$_3$ | CH$_3$ | A | 197-8 | +90° | C$_{28}$H$_{37}$FO$_9$ | 536.6 | 99.8 |
| 6b | F | H | β | COCH$_2$CH$_3$ | CH$_3$ | B | 218-21 | ±0° | C$_{28}$H$_{37}$FO$_9$ | 536.6 | 99.8 |
| 7a | F | H | β | COCH$_2$CH$_3$ | CH$_2$CH$_2$CH$_3$ | A | 135-9 | +79.6° | C$_{30}$H$_{41}$FO$_9$ | 564.7 | 93.7 |
| 7b | F | H | β | COCH$_2$CH$_3$ | CH$_2$CH$_2$CH$_3$ | B | 208-9 | ±0° | C$_{30}$H$_{41}$FO$_9$ | 564.7 | 99.3 |
| 8a | F | H | β | COCH$_2$CH$_3$ | CH(CH$_3$)$_2$ | A | 176-8 | +83.3° | C$_{30}$H$_{41}$FO$_9$ | 564.7 | 99.0 |

TABLE 1-continued

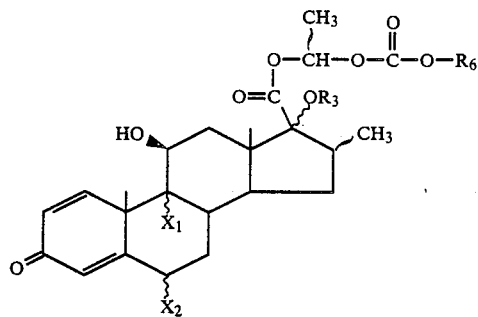

| Ex. No. | $X_1$ | $X_2$ | 16-Me | $R_3$ | $R_6$ | Epimer | M.p. °C. | $[\alpha]_D^{25}$ (c = 0.2 in $CH_2Cl_2$) | Empirical formula | Mol. weight | HPLC % purity |
|---|---|---|---|---|---|---|---|---|---|---|---|
| 8b | F | H | β | $COCH_2CH_3$ | $CH(CH_3)_2$ | B | 242-5 | ±0° | $C_{30}H_{41}FO_9$ | 564.7 | 99.4 |
| 9a | F | H | β | $COCH_2CH_3$ | $CH_2CH=CH_2$ | A | 158-60 | +84.2° | $C_{30}H_{39}FO_9$ | 562.6 | 99.4 |
| 9b | F | H | β | $COCH_2CH_3$ | $CH_2CH=CH_2$ | B | 191-207 | +5.1° | $C_{30}H_{39}FO_9$ | 562.6 | 99.1 |
| 10a | F | H | β | $COCH_2CH_3$ | $CH_2CH(CH_3)_2$ | A | 156-8 | +81° | $C_{31}H_{43}FO_9$ | 578.7 | 99.7 |
| 10b | F | H | β | $COCH_2CH_3$ | $CH_2CH(CH_3)_2$ | B | 205-8 | +0.5° | $C_{31}H_{43}FO_9$ | 578.7 | 99.7 |
| 11a | F | H | β | $COCH_2CH_3$ | $CH_2(CH_2)_6CH_3$ | A | 97-100 | +77.7° | $C_{35}H_{51}FO_9$ | 634.8 | 99.7 |
| 11b | F | H | β | $COCH_2CH_3$ | $CH_2(CH_2)_6CH_3$ | B | 139-42 | +3.3° | $C_{35}H_{51}FO_9$ | 634.8 | 99.8 |
| 12a | F | H | β | $COCH_2CH_3$ | $CH_2CH(CH_2)_2$ | A | 175-7 | +89.8° | $C_{31}H_{41}FO_9$ | 576.7 | 99.6 |
| 12b | F | H | β | $COCH_2CH_3$ | $CH_2CH(CH_2)_2$ | B | 205-7 | ±0° | $C_{31}H_{41}FO_9$ | 576.7 | 99.7 |
| 13a | F | H | β | $COCH_2CH_3$ | $CH(CH_2)_3$ | A | 157-61 | +78.5° | $C_{31}H_{41}FO_9$ | 576.7 | 99.4 |
| 13b | F | H | β | $COCH_2CH_3$ | $CH(CH_2)_3$ | B | 203-16 | −1.9° | $C_{31}H_{41}FO_9$ | 576.7 | 99.3 |
| 14a | F | H | β | $COCH_2CH_3$ | $CH(CH_2)_4$ | A | 202-7 | +75.5° | $C_{32}H_{43}FO_9$ | 590.7 | 99.1 |
| 14b | F | H | β | $COCH_2CH_3$ | $CH(CH_2)_4$ | B | 222-5 | +3.8° | $C_{32}H_{43}FO_9$ | 590.7 | 99.6 |
| 15a | F | H | β | $COCH_2CH_3$ | $CH(CH_2)_5$ | A | 194-200 | +83.5° | $C_{33}H_{45}FO_9$ | 604.7 | 99.6 |
| 15b | F | H | β | $COCH_2CH_3$ | $CH(CH_2)_5$ | B | 209-18 | ±0° | $C_{33}H_{45}FO_9$ | 604.7 | 99.7 |
| 16a | F | H | β | $COCH_2CH_3$ | $CH_2C(CH_3)=CH_2$ | A | 144-6 | +75.2° | $C_{31}H_{41}FO_9$ | 576.7 | 99.4 |
| 16b | F | H | β | $COCH_2CH_3$ | $CH_2C(CH_3)=CH_2$ | B | 188-92 | +3.4° | $C_{31}H_{41}FO_9$ | 576.7 | 98.9 |
| 17a | F | H | β | $COCH_2CH_3$ | $CH_2CCl_3$ | A | 222-5 | — | $C_{29}H_{36}Cl_3FO_9$ | 653.7 | 97.1 |
| 17b | F | H | β | $COCH_2CH_3$ | $CH_2CCl_3$ | B | 203-5 | — | $C_{29}H_{36}Cl_3FO_9$ | 653.7 | 97.8 |
| 18a | F | H | β | $COCH_2CH_3$ | $CH_2CH_2Cl$ | A | 168-80 | +74.3° | $C_{29}H_{38}ClFO_9$ | 585.1 | 97.0 |
| 18b | F | H | β | $COCH_2CH_3$ | $CH_2CH_2Cl$ | B | 194-96 | +7.5° | $C_{29}H_{38}ClFO_9$ | 585.1 | 99.5 |
| 19a | F | H | β | $COCH_2CH_3$ | $CH_2C_6H_4NO_2$ | A | — | +56.1° | $C_{34}H_{40}FNO_{11}$ | 657.7 | 99.5 |
| 19b | F | H | β | $COCH_2CH_3$ | $CH_2C_6H_4NO_2$ | B | 210-2 | +3.5° | $C_{34}H_{40}FNO_{11}$ | 657.7 | 99.5 |
| 20a | F | H | β | $COCH_2CH_3$ | $C_6H_5$ | A | 190-5 | +109.7° | $C_{33}H_{39}FO_9$ | 598.7 | 99.6 |
| 20b | F | H | β | $COCH_2CH_3$ | $C_6H_5$ | B | 199-207 | −19.0° | $C_{33}H_{39}FO_9$ | 598.7 | 99.7 |
| 21a | F | H | β | $CO(CH_2)_3CH_3$ | $CH_2CH_3$ | A | 117-9 | +81.7° | $C_{31}H_{43}FO_9$ | 578.7 | 99.8 |
| 21b | F | H | β | $CO(CH_2)_3CH_3$ | $CH_2CH_3$ | B | 172-5 | −0.5° | $C_{31}H_{43}FO_9$ | 578.7 | 99.2 |
| 22a | F | H | β | $CO(CH_2)_3CH_3$ | $CH(CH_3)_2$ | A | 155-6 | +81.1° | $C_{32}H_{45}FO_9$ | 592.7 | 99.7 |
| 22b | F | H | β | $CO(CH_2)_3CH_3$ | $CH(CH_3)_2$ | B | 168-70 | −0.5° | $C_{32}H_{45}FO_9$ | 592.7 | 99.7 |
| 23 | F | H | β | H | $CH(CH_3)_2$ | A + B | — | — | $C_{27}H_{37}FO_8$ | 508.6 | 99.4 |
| 24a | F | H | α | $COCH_2CH_3$ | $CH_2CH_3$ | A | 191-2 | +65.2° | $C_{29}H_{39}FO_9$ | 550.6 | 99.9 |
| 24b | F | H | α | $COCH_2CH_3$ | $CH_2CH_3$ | B | 218-9 | −23.3° | $C_{29}H_{39}FO_9$ | 550.6 | 99.7 |
| 25a | F | H | α | $COCH_2CH_3$ | $C(CH_3)_3$ | A | 106-17 | +64.4° | $C_{31}H_{48}FO_9$ | 578.7 | 99.6 |
| 25b | F | H | α | $COCH_2CH_3$ | $C(CH_3)_3$ | B | 117.9 | −22.1° | $C_{31}H_{43}FO_9$ | 578.7 | 99.0 |
| 26a | F | F | α | $COCH_2CH_3$ | $CH_2CH_3$ | A | 231-4 | — | $C_{29}H_{38}F_2O_9$ | 568.6 | 99.5 |
| 26b | F | F | α | $COCH_2CH_3$ | $CH_2CH_3$ | B | 229-31 | — | $C_{29}H_{38}F_2O_9$ | 568.6 | 99.7 |
| 27a | F | F | α | $COCH_2CH_3$ | $CH(CH_3)_2$ | A | 200-10 | +61.3° | $C_{30}H_{40}F_2O_9$ | 582.6 | 99.7 |
| 27b | F | F | α | $COCH_2CH_3$ | $CH(CH_3)_2$ | B | 240-44 | −22.1° | $C_{30}H_{40}F_2O_9$ | 582.6 | 99.8 |
| 28a | Cl | H | β | $COCH_2CH_3$ | $CH_2CH_3$ | A | 186-97 | +96.0° | $C_{29}H_{39}ClO_9$ | 567.1 | 99.6 |
| 28b | Cl | H | β | $COCH_2CH_3$ | $CH_2CH_3$ | B | 189-96 | +23.0° | $C_{29}H_{39}ClO_9$ | 567.1 | 99.6 |
| 29a | Cl | H | β | $COCH_2CH_3$ | $CH_2CH_2CH_3$ | A | 184-6 | +98.5° | $C_{30}H_{41}ClO_9$ | 581.1 | 99.3 |
| 29b | Cl | H | β | $COCH_2CH_3$ | $CH_2CH_2CH_3$ | B | — | +17.3° | $C_{30}H_{41}ClO_9$ | 581.1 | 99.3 |
| 30a | Cl | H | β | $COCH_2CH_3$ | $CH(CH_2)_3$ | A | 151-5 | +101.5° | $C_{31}H_{41}ClO_9$ | 593.1 | 99.7 |
| 30b | Cl | H | β | $COCH_2CH_3$ | $CH(CH_2)_3$ | B | 119-23 | +19.8° | $C_{31}H_{41}ClO_9$ | 593.1 | 99.5 |
| 31a | Cl | H | β | $COCH_2CH_3$ | $CH(CH_3)_2$ | A | 217-8 | 103.5° | $C_{30}H_{41}ClO_9$ | 581.1 | 99.7 |
| 31b | Cl | H | β | $COCH_2CH_3$ | $CH(CH_3)_2$ | B | 172-3 | — | $C_{30}H_{41}ClO_9$ | 581.1 | 99.6 |
| 32a | Cl | H | β | $COCH_2CH_3$ | $CH_2CH(CH_2)_2$ | A | 181-6 | +108.9° | $C_{31}H_{41}ClO_9$ | 593.1 | 99.8 |
| 32b | Cl | H | β | $COCH_2CH_3$ | $CH_2CH(CH_2)_2$ | B | 130-3 | +22.8° | $C_{31}H_{41}ClO_9$ | 593.1 | 99.8 |

TABLE 2

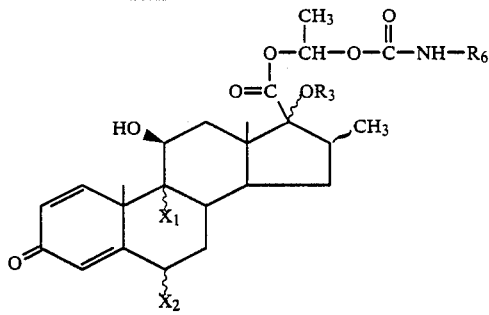

| Ex. No. | $X_1$ | $X_2$ | 16-Me | $R_3$ | $R_6$ | Epimer | M.p. °C. | Empirical formula | Mol. weight | HPLC % purity |
|---|---|---|---|---|---|---|---|---|---|---|
| 33a | F | H | β | $CH_2CH_3$ | $CH(CH_2)_2$ | A | 126–130 | $C_{30}H_{40}FNO_8$ | 561.7 | 96.2 |
| 33b | F | H | β | $CH_2CH_3$ | $CH(CH_2)_2$ | B | 136–9 | $C_{30}H_{40}FNO_8$ | 561.7 | 98.8 |

EXAMPLE 34

Pharmaceutical preparations

The following non-limitative examples illustrate formulations intended for different topical forms of administration. The amount of active steroid in the percutaneous formulations are ordinarily 0.001–0.2% (w/w), preferably 0.01–0.1% (w/w).

| Formulation 1, Ointment | |
|---|---|
| Steroid, micronized | 0.025 g |
| Liquid paraffin | 10.0 g |
| White soft paraffin | ad 100.0 g |
| Formulation 2, Ointment | |
| Steroid | 0.025 g |
| Propylene glycol | 5.0 g |
| Sorbitan sesquioleate | 5.0 g |
| Liquid paraffin | 10.0 g |
| White soft paraffin | ad 100.0 g |
| Formulation 3, Oil in water cream | |
| Steroid | 0.025 g |
| Cetanol | 5.0 g |
| Glyceryl monostearate | 5.0 g |
| Liquid paraffin | 10.0 g |
| Cetomacrogol 1000 | 2.0 g |
| Citric acid | 0.1 g |
| Sodium citrate | 0.2 g |
| Propylene glycol | 35.0 g |
| Water | ad 100.0 g |
| Formulation 4, Oil in water cream | |
| Steroid, micronized | 0.025 g |
| White soft paraffin | 15.0 g |
| Liquid paraffin | 5.0 g |
| Cetanol | 5.0 g |
| Sorbimacrogol stearate | 2.0 g |
| Sorbitan monostearate | 0.5 g |
| Sorbic acid | 0.2 g |
| Citric acid | 0.1 g |
| Sodium citrate | 0.2 g |
| Water | ad 100.0 g |
| Formulation 5, Water in oil cream | |
| Steroid | 0.025 g |
| White soft paraffin | 35.0 g |
| Liquid paraffin | 5.0 g |
| Sorbitan sesquioleate | 5.0 g |
| Sorbic acid | 0.2 g |
| Citric acid | 0.1 g |
| Sodium citrate | 0.2 g |
| Water | ad 100.0 g |
| Formulation 6, Lotion | |
| Steroid | 0.25 mg |
| Isopropanol | 0.5 ml |
| Carboxyvinylpolymer | 3 mg |
| NaOH | q.s. |
| Water | ad 1.0 g |

| -continued | |
|---|---|
| Formulation 7, Suspension for injection | |
| Steroid, micronized | 0.05–10 mg |
| Sodium carboxymethylcellulose | 7 mg |
| NaCl | 7 mg |
| Polyoxyethylene (20) sorbitan monooleate | 0.5 mg |
| Phenyl carbinol | 8 mg |
| Water, sterile | ad 1.0 ml |
| Formulation 8, Aerosol for oral and nasal inhalation | |
| Steroid, micronized | 0.1% w/w |
| Sorbitan trioleate | 0.7% w/w |
| Trichlorofluoromethane | 24.8% w/w |
| Dichlorotetrafluoromethane | 24.8% w/w |
| Dichlorodifluoromethane | 49.6% w/w |
| Formulation 9, Solution for atomization | |
| Steroid | 7.0 mg |
| Propylene glycol | 5.0 g |
| Water | ad 10.0 g |
| Formulation 10, Powder for inhalation | |
| A gelatin capsule is filled with a mixture of Steroid, micronized | 0.1 mg |
| Lactose | 20 mg |

The powder is inhaled by means of an inhalation device.

PHARMACOLOGY

The affinity of the new androstane-17β-carboxylic acid esters of the glucocorticoid receptor All steroids according to the present invention are physiologically active compounds. The affinity of the novel androstane-17β-carboxylic acid esters to the glucocorticoid receptor has been used as a model for determination of the anti-inflammatory potency. Their receptor affinities have been compared to budesonide ([22R,S]-16α, 17α-butylidenedioxy-11β,21-dihydroxypregna-1,4-diene-3,20-dione) a highly active glucocorticoid with a favourable ratio between local and systemic effects (Thalén and Brattsand, Arzneim.-Forsch. 29, 1687–90 (1979)).

Male Sprague-Dawley rats, one to two months of age, were used throughout the investigation. The thymus was removed and put into ice-cold saline. The tissue was homogenized in a Potter Elvehjem homogenizer in 10 ml of a buffer containing 20 mM Tris, pH 7.4, 10% (w/v) glycerol, 1 mM EDTA, 20 mM $NaMoO_4$, 10 mM mercaptoethanol. The homogenate was centrifuged for 15 min at 20,000×g. Portions of the 20,000×g supernatant (230 μl) were incubated for about 24 h at 0°

C. with 100 μl phenylmethylsulphonylfluoride (an esterase inhibitor, final conc. 0.5 mM), 20 μl unlabelled competitor and 50 μl $^3$H-labelled dexamethasone (final conc. 3 nM). Bound and free steroid were separated by incubating the mixture with 60 μl 2.5% (w/v) charcoal and 0.25% (w/v) dextran T70 suspension in 20 nM Tris, pH 7.4, 1 mM EDTA, and 20 nM NaMoO$_4$ for 10 min at 0° C. Following a centrifugation at 500×g for 10 min, 230 μl of the supernatant was counted in 10 ml Insta-Gel in a Packard scintillation spectrophotometer. The supernatants were incubated with a) [$^3$H]dexamethasone alone, b) [$^3$H] dexamethasone plus 1000 fold excess of unlabelled dexamethasone and c) [$^3$H] dexamethasone plus 0.03–300 fold "excess" competitor. The nonspecific binding was determined when 1000 fold excess of unlabelled dexamethasone was added to [$^3$H]-labelled dexamethasone.

The radioactivity bound to the receptor in the presence of competitor divided by the radioactivity bound to the receptor in the absence of competitor multiplied by 100 gives the percentage specific binding of labelled dexamethasone. For each concentration of a competitor the percentage specifically bound radioactivity is plotted against the log of concentration of competitor. The curves are compared at the 50% specific binding level and reference to budesonide, which is assigned a relative binding affinity (RBA) of 1.

| Compound according to the example no. | RBA |
|---|---|
| Budesonide | 1 |
| 1 (epimer B) | 0.80 |
| 2 (epimer B) | 0.14 |
| 3 (epimer B) | 0.47 |
| 4 (epimer B) | 0.69 |
| 6b | 0.42 |
| 7b | 0.95 |
| 8b | 1.50 |
| 9b | 0.39 |
| 10b | 0.82 |
| 13b | 1.3 |
| 14b | 1.2 |
| 15b | 0.54 |
| 16b | 0.51 |
| 19b | 0.53 |
| 22b | 0.77 |
| 24b | 0.55 |
| 26b | 0.45 |
| 28b | 1.0 |
| 32b | 0.86 |

We claim:
1. A compound of the formula

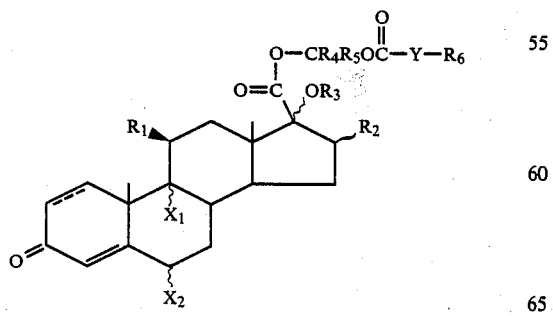

or a stereoisomeric component thereof, in which formula $X_1$ represents a hydrogen, chlorine, bromine or fluorine atom;

$X_2$ represents a hydrogen, chlorine, bromine or fluorine atom;

$R_1$ represents a β-hydroxy group, a β-chlorine atom or an oxo group;

$R_2$ represents a hydrogen atom, a methylene group or an α- or β-methyl group;

$R_3$ represents a hydrogen atom or an acyl group of 1 to 8 carbon atoms;

$R_4$ represents a hydrogen atom, a ($C_1$–$C_5$) alkyl group or a phenyl group;

$R_5$ represents a hydrogen atom, a ($C_1$–$C_5$) alkyl group or a phenyl group;

Y represents either $CR_7R_8$, O, S or $NR_9$, where $R_7$, $R_8$ and $R_9$ are selected from hydrogen or from straight or branched hydrocarbon chains having 1-8 carbon atoms or from a phenyl group;

$R_6$ represents a hydrogen; a methyl group; a phenyl or an alkenyl or cycloalkenyl group optionally substituted by alkyl, nitro, carboxy, alkoxy, halogen, cyano, carbalkoxy and trifluoromethyl group(s); a ($C_1$–$C_5$) alkyl group substituted by at least one hydrogen atom; a saturated or unsaturated carbocyclic or heterocyclic (O, S, N) ring system containing 3-10 atoms in the ring system; a $C_1$ alkyl group substituted by either one or two alicyclic or aromatic 3, 4, 5 or 6-numbered ring system(s) or one, two or three straight or branched alkyl or alkenyl group(s) of 1 through 18 carbon atoms; and ⎓ represents a single or double bond.

2. A compound according to claim 1, wherein
$X_1$ is a fluorine or chlorine atom;
$X_2$ is a fluorine or chlorine atom;
$R_1$ is a β-hydroxy group;
$R_3$ is an acetyl, propionyl, butyryl or valeroyl group;
$R_4/R_5$ is hydrogen/methyl or methyl/hydrogen;
Y is O;
$R_6$ is an alkyl group containing 1-5 carbon atoms, and
⎓ represents a double bond.

3. A pharmaceutical preparation according to claim 1 comprising the active ingredient in association with a pharmaceutically acceptable carrier.

4. A pharmaceutical preparation according to claim 3 in dosage unit form.

5. A method for the treatment of control of inflammatory conditions in mammals, including man, characterized by the administration to a host in need of such treatment of an effective amount of a compound according to claim 1.

6. A process for the preparation of a compound of the formula

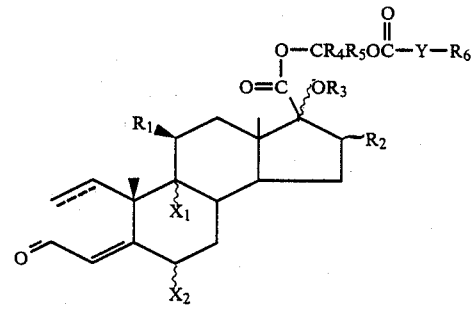

or a stereoisomeric component thereof, in which formula $X_1$ represents a hydrogen, chlorine, bromine or fluorine atom;

$X_2$ represents a hydrogen, chlorine, bromine or fluorine atom;

$R_1$ represents a -hydroxy group, a -chlorine atom an oxo group;

$R_2$ represents a hydrogen atom, a methylene group or an — or -methyl group;

$R_3$ represents a hydrogen atom or an alkanoyl group of 1 through 8 carbon atoms;

$R_4$ represents a hydrogen atom, a ($C_1$-$C_5$) alkyl group or a phenyl group;

$R_5$ represents a hydrogen atom, a ($C_1$-$C_5$) alkyl group or a phenyl group;

Y represents either $CR_7R_8$, O, S or $NR_9$, where $R_7$, $R_8$ and $R_9$ are selected from hydrogen or from straight or branched hydrocarbon chains having 1-8 carbon atoms or from a phenyl group;

$R_6$ represents a hydrogen; a methyl group; a phenyl or an alkenyl or cycloalkenyl group optionally substituted by alkyl, nitro, carboxy, alkoxy, halogen, cyano, carbalkoxy and trifluoromethyl group(s); a ($C_1$-$C_5$) alkyl group substituted by at least one halogen atom; a saturated or unsaturated carbocyclic or heterocyclic (O, S, N) ring system containing 3-10 atoms in the ring system; a $C_1$ alkyl group substituted by either one or two alicyclic or aromatic 3, 4, 5 or 6-numbered ring system(s) or one, two or three straight or branched alkyl or alkenyl group(s) of 1 through 18 carbon atoms; and $\rule{1em}{0.1pt}$ represents a single or double bond, characterised by reaction of a compound of the formula

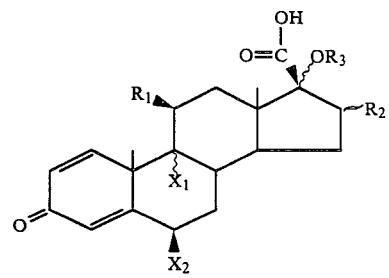

or a salt thereof with a compound of the formula

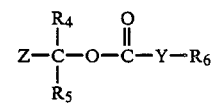

in which formulas $X_1$, $X_2$, $R_1$, $R_2$, $R_3$, $R_4$, $R_5$, $R_6$, Y and $\rule{1em}{0.1pt}$ have the same meaning as above and Z is a halogen atom or a functionally equivalent group.

7. A process according to claim 6 wherein a compound according to claim 2 is prepared.

8. A compound of the formula

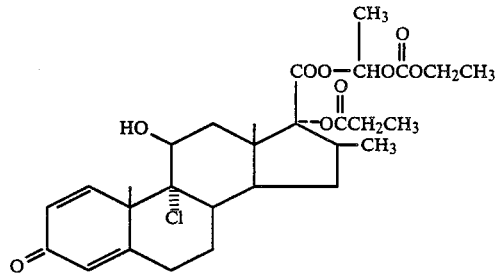

* * * * *

UNITED STATES PATENT AND TRADEMARK OFFICE
CERTIFICATE OF CORRECTION

PATENT NO. : 4,804,656
DATED : February 14, 1989
INVENTOR(S) : Paul H. Andersson et al.

It is certified that error appears in the above-identified patent and that said Letters Patent is hereby corrected as shown below:

First page, 16th-from-bottom line of ABSTRACT, "cycloalkylene" should read --cycloalkenyl--;

First page, 5th-from-bottom line of ABSTRACT, before "represents" insert -- ___ --;

Col. 1, line 24, "THe" should read --The--;

Col. 2, line 8, "of" should read --or--

Col. 3, line 9, "designed" should -- read designated--

Col. 5, line 55, "99.3% p" should read --99.3%;--;

Col. 6, line 41, "of a" should read --of--

Col. 6, line 57, vakuum" should read --vacuum--

Col 7, line 4, "vakuum" should read --vacuum--

Col. 7, line 5, "in" should read --and--

UNITED STATES PATENT AND TRADEMARK OFFICE
CERTIFICATE OF CORRECTION

PATENT NO. : 4,804,656

DATED : February 14, 1989

INVENTOR(S) : Paul H. Hendersson et al.

It is certified that error appears in the above-identified patent and that said Letters Patent is hereby corrected as shown below:

Col. 8, line 14, "zinkchloride" should read --zinc chloride--;

Col. 8, line 41, "$M^+$" should read --$MH^+$--;

Col. 8, TABLE 1, first line under heading "$R_3$", "$COCH_2CH_3$" should read --$COCH_3CH_3$--;

Col. 10, penultimate line, last col., "99.8" should read --99.7--;

Col. 12, lines 38-39, "0.1 mg" should appear on the same line with "Steroid, micronized";

Col. 12, line 47, "esters of" should read --esters to--;

Col. 13, line 14, after " "excess" " insert --of--;

Col. 14, line 48, "of control" should read --and control--;

UNITED STATES PATENT AND TRADEMARK OFFICE
CERTIFICATE OF CORRECTION

PATENT NO. : 4,804,656  Page 3 of 4
DATED : February 12, 1989
INVENTOR(S) : Paul H. Andersson et al.

It is certified that error appears in the above-identified patent and that said Letters Patent is hereby corrected as shown below:

Col. 14, line 55,

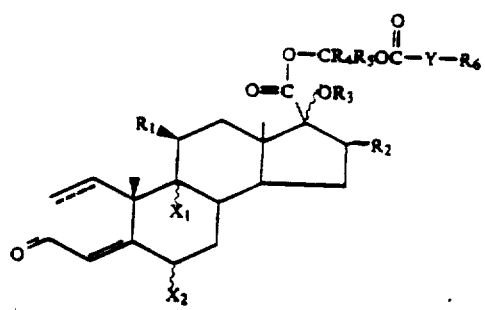

should read

-- 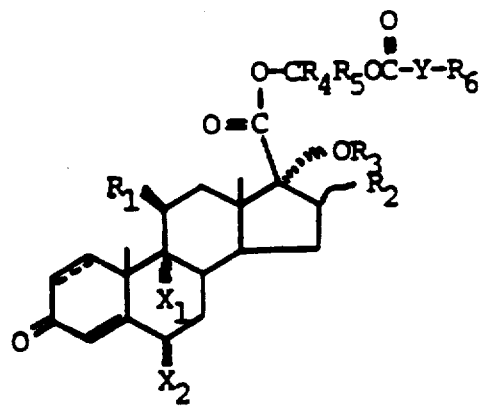 --

UNITED STATES PATENT AND TRADEMARK OFFICE
CERTIFICATE OF CORRECTION

PATENT NO. : 4,804,656
DATED : February 14, 1989
INVENTOR(S) : Paul H. Andersson et al.

It is certified that error appears in the above-identified patent and that said Letters Patent is hereby corrected as shown below:

Col. 15, line 8, "-hydroxy group, a -chlorine" should read --β-hydroxy group, a β-chlorine;

Col. 15, line 12, "——or -methyl" should read --α- or β-methyl--

Col. 16, line 7, [the straight line checked should be dashes] AND the 'pyramid" should be a squiggle Col. 16, line 30, that portion of the formula reading ":" should read --¦--.

Signed and Sealed this

Third Day of April, 1990

Attest:

HARRY F. MANBECK, JR.

Attesting Officer

Commissioner of Patents and Trademarks